United States Patent [19]

Hung

[11] Patent Number: 4,743,619
[45] Date of Patent: May 10, 1988

[54] METHOD OF TREATING HEPATITIS

[75] Inventor: Paul P. Hung, Bryn Mawr, Pa.

[73] Assignee: American Home Products Corporation, New York, N.Y.

[21] Appl. No.: 900,012

[22] Filed: Aug. 25, 1986

Related U.S. Application Data

[63] Continuation-in-part of Ser. No. 770,807, Aug. 29, 1985, Pat. No. 4,631,290.

[51] Int. Cl.$^4$ .............. A61U 31/21; A61U 31/26; A61K 39/12; A61K 39/29
[52] U.S. Cl. ............................ 514/450; 424/85; 424/114; 514/894; 514/473; 514/468
[58] Field of Search .............. 514/450, 894, 473, 468; 424/85, 114

[56] References Cited

U.S. PATENT DOCUMENTS

| 3,342,810 | 9/1967 | Maggi et al. | 260/239.3 |
| 3,751,567 | 8/1973 | Konopka et al. | 424/114 |
| 4,007,169 | 2/1977 | Marsili et al. | 260/239.3 P |
| 4,017,481 | 4/1977 | Marsili et al. | 260/239.3 P |
| 4,327,096 | 4/1982 | Marsili et al. | 514/468 |

OTHER PUBLICATIONS

Green, et al., Proc. Nat'l. Acad. Sc. (P.N.A.S.), 69, 1294-98 (1972).
Thompson, et al., P.N.A.S., 71, 107-9 (1974).
Wu, et al., P.N.A.S., 70, 1298-1302 (1973).
Gurgo et al., J. Nat'l. Cancer Inst., 49, 61-79 (1972).
Smith and Robinson, et al., J. Infect. Dis., 48, 907-13 (1983).
Kaplan, et al., J. Virol., 12, 995-1005 (1973).
Landers et al., J. Virol., 23, 368-376 (1977).
Summers and Mason, Cell., 29, 403-415 (1982).
Toh et al., Nature, 305, 827-829 (1983).
Summers, Hepatology, 1, 179-183 (1980).
Beasley and Hwang, Chapt. 16, pp. 209-224, in G. N. Vyas et al., Eds., Viral Hepatitis and Liver Disease, (Grune & Stratton, Inc., Orlando (1984)).
Gitlin, Chapt. 8, pp. 115-122, in G. N. Vyas et al., Eds, above: [AV].
Hoofnagle and Alter, Chapt. 7, pp. 97-114, in Vyas et al., Eds, above [AV].
Marion, et al., P.N.A.S., 77, 2941-2945 (1980).
Robinson, Am. J. Med. Sci. 270, 151-159 (1975).
Derwent Abst. 46957 D/26 (Jpn. Kokai No. J56053-682 (5/1981)).
Chem. Abst. No. 92:58837u (Jpn. Kokai No. 79, 112, 898 (9/1979)).
Chem. Abst. No. 94:65736e (Jpn. Kokai No. 80 89, 286 (7/1980)).
Chem. Abst. No. 91:20555s (Jpn. Kokai No. 78 149,999 (12/1978)).
Fowler et al., J. Med. Virology, 13, 83-91 (1984).
Summers et al., P.N.A.S., 72, 4597-4601 (1975).

*Primary Examiner*—Ronald W. Griffin
*Attorney, Agent, or Firm*—Arthur G. Seifert

[57] ABSTRACT

The invention disclosed herein provides a method of treating an animal infected by hepatitis B virus comprising administering to such infected animal an amount of a rifamycin derivative selected from a group consisting of (a) 3-amino-4-deoxo-4-imino-rifamycin S,
(b) 3-amino-4-deoxo-4-[(4-aminophenyl)sulfonyl]amino-rifamycin SV,
(c) 4-O-(n-butylsulfonyl)-3-[(1-piperidinylimino)methyl]-rifamycin SV,
(d) 4-O-(n-butylsulfonyl)-3-[(4-morpholinylimino)methyl]-rifamycin SV,
(e) 3-[(dimethylhydrazono)methyl]-4-O-[(3-phenylpropyl)sulfonyl]-rifamycin SV, and
(f) 4-deoxo-N,3-ethylidenimino-4-(methylsulfonyl)amino-rifamycin SV, said amount being effective to alleviate the effects of said hepatitis B virus. Also disclosed is a method of inhibiting the viral polymerase of hepatitis B virus by subjecting said polymerase to an amount of one of the rifamycin derivatives (a)-(f) above, said amount being effective to prevent the synthesis of hepatitis B virus by said viral polymerase. Compounds (b)-(f) described above are novel compounds.

7 Claims, No Drawings

METHOD OF TREATING HEPATITIS

This application is a continuation-in-part of co-pending U.S. patent application Ser. No. 770,807, filed Aug. 29, 1985, now U.S. Pat. No. 4,631,290, issued Dec. 23, 1986.

Hepatitis caused by hepatitis B virus (HBV) is one of the last few major diseases which has not been effectively controlled. No effective treatment or preventative agent has yet been found for this disease. Applicant's invention pertains to a method of treating and preventing hepatitis caused by hepatitis B virus utilizing certain rifamycia S and SV derivatives.

BACKGROUND OF THE INVENTION

Hepatitis B virus (HBV) is prevalent throughout the world, but is especially endemic to parts of Asia and Africa. Acute infection is usually resolved after 4-6 months; however, chronic infection often lasts a lifetime and is highly associated, inter alia, with the development of cirrhosis and primary hepatocellular carcinoma. See, for example, Beasley and Hwang, "Epidimiology of Hepatocellular Carcinoma," Chapter 16, pp. 209-224 in Vyas, Girish N. et al., eds., *Viral Hepatitis and Liver Disease*, (Grune and Stratton, Inc., Orlando, Fla., 1984), where it is reported that, on a worldwide basis, 80 percent of the people in whom primary hepatocellular carcinoma occurs are hepatitis B surface antigen (HBsAg) carriers. The 200 million chronic HBV carriers worldwide can act as a reservoir of infectious HBV in the general population. Accordingly, the development of an effective treatment of hepatitis B viral infections, especially of chronic hepatitis, is urgently needed to arrest the increasing spread of this disease.

Chronic HBV infection can be categorized into chronic active hepatitis (CAH) and chronic persistent hepatitis. CAH symptoms encompass fatigue, nausea, anorexia and/or abdominal pain, and general depression of liver function. Chronic persistent HBV infection is associated with cirrhosis of the liver. As noted above, acute HBV infection is usually resolved in 4-6 months. Its symptoms encompass fever, malaise, fatigue, anorexia, nausea, vomiting and abdominal pain. A small portion of acute HBV infections result in massive hepatic necrosis, coma, and death. No chemotherapeutic agent has yet been found to be effective for treatment of acute viral hepatitis (Vyas, Girish N. et al., eds., above, Chapter 8, pp. 115-122, at page 115).

Ideally, antiviral agents for HBV infection could be used to eliminate HBV infection from chronic carriers, thus decreasing their changes of developing HBV associated cirrhosis and primary heptocellular carcinoma. In addition, antiviral agents could be used to speed up recovery from acute HBV infection. At present no such chemotherapeutic agent has been identified. The development of such antiviral agents has been hindered by three major factors. First, the host range of HBV appears to be confined to humans, the natural host, and a few higher primates such as chimpanzees. Although three related viruses which infect the Beechey ground squirrel (Ground Squirrel Hepatitis Virus GSHV), the woodchuck (Woodchuck Heptatitis Virus: WHV) and the domestic duck (Duck Heptatitis B Virus: DHBV), have been found, none of these viruses can infect nor replicate in common laboratory animals such as rats and mice (Summers, Hepatology 1: 179-183, 1980). Secondly, no laboratories have been able to infect and propagate HBV in tissue culture. Recently, Tuttleman et al (Molecular Biology of Hepatitis B Viruses, Cold Spring Harbor Labs, pg. 9, 1985) have described a tissue culture system in which 5% primary duck hepatocytes can be infected with the duck hepatitis B virus (DHBV), a member of the hepatitis B virus family. However, since the protocol utilizes normal hepatocytes from young ducklings, the system cannot be readily adapted for propagation of HBV in human hepatocytes (i.e., lack of donor hepatocytes). Thirdly, the study of the mechanism of replication of HBV, characterization of the viral gene products, and elucidation of factors which influence the outcome of the infection has progressed slowly due to the aforementioned factors.

In spite of these obstacles, there have been attempts at and partial success in providing a method of treatment of hepatitis B virus by chemotherapy and/or immunotherapy. However, a practical, effective treatment for hepatitis B virus infection has not been found. One such attempt and partial success is described by C. I. Smith and William S. Robinson, et al., "Acute Dane Particle Suppression with Recombinant Leukocyte A Interferon in Chronic Hepatitis B Virus Infection," The Journal of Infectious Diseases, 148, 907-13 (1983). In this method Robinson and his coworkers used a leukocyte A Interfereon (rINF-A or HuIFN-2), produced by recombinant DNA methods, to treat nine patients with chronic hepatitis B virus infection. They report that most courses of rINF-A treatment were associated with a reduction in polymerase activity of the viron or Dane particle. However, this change was not permanent in any of the patients.

One means of developing an effective treatment for HBV infection is to invent a compound which inhibits the function of a particular viral protein which is necessary for viral replication, such as a viral-associated polymerase. Robinson and colleagues discovered a polymerase inside the HBV particles isolated from serum (Kaplan, et al., J. Virol 12: 995-1005, 1973). Its presence can be readily detected by the endogenous polymerase assay which measures the ability of the polymerase to incorporate radiolabeled nucleotides into the viral genome. Further studies showed that only one strand, called the short strand or +strand was being synthesized in each particle (Summers et al, Proc. Nat'l. Acad. Science 72, 4597-4601, 1975; Landers et al., J. Virol. 23, 368-376, 1977). Using the related duck hepatitis B virus animal model, Summers and Mason (Cell 29, 403-413, 1982) have isolated immature viral particles from infected duck hepatocytes and showed that (1) the RNA pregenome was packaged in immature particles, (2) an endogenous polymerase synthesized the minus strand DNA from the RNA template by reverse transcription (3) the RNA template was degraded by an RNAse H activity present in the particles, (4) the plus strand was synthesized using the minus (−) strand DNA as a template, and (5) the polymerase associated with the immature viral particles did exhibit reverse transcriptase-like activity. Recent studies of HBV, GSHV, and WHV DNA intermediates isolated from infected liver revealed asymmetric synthesis of minus strand, consistent with the above findings (Weiser et al., J. Virol. 48, 1-9, 1983; Fowler et al., J. Med. Virol. 13, 83-91, 1984; Roggendorf and Summers, Molecular Biology of Hepatitis B Viruses, Cold Spring Harbor Laboratories, pg. 5, 1985). Although no laboratory has directly shown that the polymerase found in the viral particles is encoded by the virus itself, Toh et al (Nature 305, 827–829, 1983) have reported the existence of extensive amino acid sequence homology in specific regions of a large open reading frame encoded by HBV (adr strain) and WHV and three other retroviral reverse transcriptases. This analysis lends some credence to the hypothesis that the reverse transcriptase associated with viral particles is encoded by the viral genome.

Since the HBV polymerase exhibits reverse transcriptase properties, one means of arriving at a method of treatment would be to test known inhibitors of similar reverse transcriptases, for example retroviral reverse transcriptases. Some rifamycin derivatives have been found to inhibit particular reverse transcriptases. The following articles disclose certain rifamycin derivatives which inhibit particular reverse transcriptases (polymerases): Maurice Green et al., "3 Cyclic Amine Derivatives of Rifamycin: Strong Inhibitors of the DNA Polymerase Activity of RNA Tumor Viruses," *Proceedings of the National Academy of Sciences (P.N.A.S.)*, 69, 1294–98 (1972); Frances M. Thompson et al., "Inhibition of Three Nucleotide Polymerases by Rifamycin Derivatives," *P.N.A.S.* 71, 107–9 (1974); Alan M. Wu, et al., "RNA Directed DNA Polymerase and Virus-Induced Leukemia in Mice," P.N.A.S. 70, 1298–1302 (1973); and Corrado Gurgo et al., "Rifamycin Derivatives strongly Inhibiting RNA DNA Polymerase (Reverse Transcriptase) of Murine Sarcoma Viruses," *Journal of the National Cancer Institute,* 49, 61–79 (1972).

Applicant herein has now surprisingly discovered a few rifamycin derivatives which inhibit the polymerase activity of hepatitis B virus. Such discovery provides means for treating hepatitis brought on by infection with hepatitis B virus.

DETAILED DESCRIPTION OF THE INVENTION

In one aspect of applicant's invention there is provided a method of treating an animal infected by hepatitis B virus comprising administering to such infected animal an amount of a rifamycin derivative selected from a group consisting of (a) 3-amino-4-deoxo-4-imino-rifamycin S,
(b) 3-amino-4-deoxo-4-[(4-aminophenyl)sulfonyl]amino-rifamycin SV,
(c) 4-O-n-(butylsulfonyl)-3-[(1-piperidinylimino)methyl]-rifamycin SV,
(d) 4-O-(n-butylsulfonyl)-3-[(4-morpholinylimino)methyl]-rifamycin SV, and
(e) 3-[(dimethylhydrazono)methyl]-4-O-[(3-phenylpropyl)sulfonyl]-rifamycin SV,
(f) 4-deoxo-N,3-ethylidenimino-4-(methylsulfonyl)amino rifamycin SV, said amount being effective to alleviate the effects of said hepatitis B virus. With regard to this aspect of the invention, the rifamycin derivative (e), namely 3-[(dimethylhydrazano)methyl]-4-O-[(3-phenylpropyl)sulfonyl]rifamycin SV is particularly preferred. The rifamycin derivative (f), namely, 4-deoxo-N,3-ethylidenimino-4-(methylsulfonyl)amino rifamycin SV, is also particularly preferred. Also preferred is an amount of such rifamycin derivative, ie. -(a)–(e), which is effective to prevent the reverse transcription of the hepatitis B virus in the infected animal. A further preferred amount of a rifamycin derivative (a)–(e) is an amount effective to show an absence of HBeAg in standard serological tests in an animal (e.g. man) previously found to be HBeAg positive. Similarly, an amount effective to show the absence of HBV-DNA or DNA polymerase where the same were present previously is also preferred.

As noted above, hepatitis B virus is presently known only to exist in man and in certain other primates and in certain animals. However, should the virus be found in other animals, some of which may act only as carriers of the disease, then the method of treatment of the invention would be applicable to such other animals also. Presently, however, "infected animal" for Applicant's method of treatment applies only to man and those animals known to be subject to the hepatitis B virus. The preferred animal for such treatment is man.

In a further aspect this invention provides a method of inhibiting the viral polymerase of hepatitis B virus, comprising subjecting said polymerase to an amount of a rifamycin derivative selected from a group consisting of (a) 3-amino-4-deoxo-4-imino-rifamycin S,
(b) 3-amino-4-deoxo-4-[(4-aminophenyl)sulfonyl]amino-rifamycin SV,
(c) 4-O-(n-butylsulfonyl)-3-[(1-piperidinylimino)methyl]-rifamycin SV,
(d) 4-O-(n-butylsulfonyl)-3-[(4-morpholinylimino)methyl]-rifamycin SV,
(e) 3-[(dimethylhydrazono)methyl]-4-O-[(3-phenylpropyl)sulfonyl]-rifamycin SV, and
(f) 4-deoxo-N,3-ethylidenimino-4-(methylsulfonyl)amino-rifamycin SV, said amount being effective to prevent the synthesis of the hepatitis B virus by said polymerase. The preferred rifamycain derivatives for this aspect of the invention are also (e) and (f) named above. This amount may be shown by a reduction in the HBV-DNA titer or DNA polymerase activity titer in standard serological tests for the same.

In another aspect, this invention provides novel compounds (b), (c), (d), (e) and (f), described above. Surprisingly, said compounds inhibit the polymerase of hepatitis B virus, according to the procedure described below, where related, known rifamycin derivatives did not show such inhibition. Compounds (e) and (f) are also preferred for this aspect of the invention.

3-amino-4-deoxo-4-imino-rifamycin S, (a) above, is described in U.S. Pat. No. 4,017,481, where it is made by reacting 3-amino-rifamycin S with gaseous ammonia. The reaction is carried out in a solution of tetrahydrofuran at room temperature for 15 hours with further addition of ammonia. The starting material, 3-amino-rifamycin S may obtained as described in U.S. Pat. No. 4,007,169, where it is obtained by reacting sodium azide with rifamycin S. The reaction is carried out in methylformamide at 35° C. for 60 minutes. The reaction mixture is diluted with methylene chloride and washed with water. The aqueous phase contains rifamycin SV which may be oxidized by, for example, nitrous acid to the starting material rifamycin S. The organic phase is washed with water, dried with sodium sulphate and evaporated to yield 3-amino rifamycin S which is recrystallized from 2-methoxy ethanol.

3-amino-4-deoxo-4-[(4-aminophenyl)sulfonyl]amino]-rifamycin SV, (b) above, may be made by reacting sodium p-analinylsulphinate with 3-amino-rifamycin S. The reaction is carried out under neutral conditions in a suitable solvent, such as dioxan at room temperature for up to 20 hours. The reaction is carried out as described in Japanese Kokai J5 6053-682 (Derwent Abstract 46957 D/26).

The 3-amino-4-deoxy-4-(methylsulfonyl)-amino rifamycin SV precursor of the compound (f) is made in the same manner as compound (b), but substituting sodium methanesulfinate for 4-aminobenzenesulfinate. Said precursor product is then reacted with acetaldehyde to form the ethylidenimino ring of final product compound (f). This two step process is illustrated in Example 5 below.

The rifamycin derivatives (c) 4-O-(n-butylsulfonyl)-3-[(1-piperidinylimino)methyl]-rifamycin SV, (d) 4-O-(n-butylsulfonyl)-3-[(4-morpholinylimino)methyl]-rifamycin SV, and (e) 3-[(dimethylhydrazono)methyl]-4-O-[(3-phenylpropyl)sulfonyl]-rifamycin SV may also be prepared in a manner described in said Japanese Kokai J5 6053-682 by reacting the appropriate 3-iminomethyl-rifamycin S derivative with an n-butylsulfonate or 3-phenylpropylsulfinate alkali metal or alkaline earth metal salt under neutral conditions.

The precursors for (c), (d) and (e) above may be made by reacting (piperidinoimino)methane, (morpholinoimino)methane, or (dimethylaminoimino)methane, respectively with rifamycin S as described in Japanese Kokai 79, 112,898, published Sept. 4, 1979 (Chem. Abstracts No. 92: 58837u). In this method the reaction is carried out in the presence of an oxidizing agent such as manganese dioxide in dimethylsulfoxide under heating (50° C.) for up to 30 hours. This method is also described in Japanese Kokai No. 80 89,286, published July 5, 1980 (Chemical Abstracts No. 94: 65736e). Another method for obtaining these 3-iminomethyl rifamycin S derivatives is described in Japanese Kokai 78, 149,999, published Dec. 27, 1978 (Chemical Abstracts No. 91: 20555s).

Other methods for making the rifamycin derivatives (a)–(e) above are known in the art, as are methods for interconverting rifamycin S and SV. For example, U.S. Pat. No. 3,342,810, discloses a method in which 3-formyl-rifamycin SV is reacted with 1-aminopiperdine, 1-methylmorpholine or dimethylaminoamine to form the desired precursor 3-iminomethyl-rifamycin SV. The preparation of 3-formyl-rifamycin SV is also described therein. It is prepared from a selected mannich base of rifamycin SV by oxidation with a weak oxidizing agent in a solvent. Such weak oxidizing agents include alkyl nitrates and lead tetracetate. Suitable mannich bases may be selected from 3-pyrrolidinomethyl, 3-dimethylaminomethyl, 3-piperidinomethyl, 3-morpholinomethyl, 3-(2,6-dimethyl)piperdinomethyl, 3-(1-methyl)-piperazinomethyl and 3-(4-carboxy)piperdinomethyl rifamycin SV, all of which are known in the art.

The ability of the rifamycin S derivatives (a)–(e) described above to inhibit the polymerase of hepatitis B virus was determined by the endogenous DNA polymerase assay according to Robinson and his colleagues as follows: In this procedure, the Dane particles were isolated from HBV-infected human blood by the method described by Landers et al., J. Virol 23: 368–376, 1977.

Ten microliters of Dane particles were incubated at 37° C. for 2 hours in 100 μl containing 0.5% NP40, 0.07% BME, 66 mM Tris HCl (pH 7.6) 27 mM MgCl$_2$, 0.40 mM NH$_4$Cl, 0.3 mM dATP, dGTP, and dTTP and 4 picomoles α$^{32}$P-dCTP. The appropriate tubes also contained either 0.1 μg/ml or 0.01 μg/ml of the rifamycin derivatives (a), (b), (c), (d), or (e). The quantity of incorporation of radioactive nucleotides into viral DNA was determined by trichloroacetic acid precipitation as described by Landers et al., J. Virol. 23: 368–376, 1977. The control DNA polymerase reaction contained more than 20,000 cpm. The results of this in vitro endogenous DNA polymerase assay for rifamycin derivatives (a)–(e) are given in Table I below:

TABLE 1

| | In Vitro Anti-viral Polymerase Activity | |
|---|---|---|
| Compound | % inhibition (0.1 μg/ml) | % inhibition (0.01 μg/ml) |
| (a) | 54.1 | 17.2 |
| (b) | 89.0 | 10.0 |
| (c) | 55.7 | 8.3 |
| (d) | 92.5 | 10.2 |
| (e) | 85.6 | 25.1 |
| (f) | 84.6 | 23.8 |

As shown in Table I, the rifamycin derivatives (a–e) inhibited the Dane particle polymerase activity ranging from 54% to 92.5% at 0.1 μg/ml. Since Summers and Mason, Cell, above, showed that the polymerase associated with the immature viral particles exhibits reverse transcriptase-like activity and Toh et al., Nature, above, showed a substantial homology between HBV and WHV polymerase and 3 other retroviral reverse transcriptases, these DNA polymerase inhibition results are consistent with an inhibitory effect on the replication of the Dane particle by the polymerase.

Clinically (in man) persistence of serum markers of viral replication, such as HBeAg, HBV-DNA and DNA polymerase activity, is usually accompanied by persistence of chronic hepatitis disease activity, and conversely, disappearance of these markers is usually followed by a remission in the chronic hepatitis. Based upon serological testing, the course of chronic heptatis B virial infection can be categorized in three outcomes (1) persistence of HBeAg (hepatitis B e antigen), HBV-DNA and DNA polymerase; (2) loss of HBeAg, HBV-DNA and DNA polymerase and seroconversion to anti-HBe; and (3) loss of HBeAg and seroconversion to anti-HBe but a subsequent reappearance of markers of HBV replication. Where (1), persistence of HBeAg, is found, persistence of the other markers of viral replication and of chronic hepatitis disease acivity (plus elevated serum aminotransferase levels (ALT)) is found. Where (2), servoconversion to anti-HBe, is found, the markers for viral replication are negative, serum ALT levels are normal and the disease is in remission. However, most of these subjects remain positive for HBsAg and are designated as "healthy" HBsAg carriers. Where (3), reactivation (known as spontaneous reactivation of hepatitis B virus), is found, intermittent symptoms of chronic hepatitis appear, during which increased ALT levels and the reappearance of HBV-DNA and DNA polymerase are observed. HBeAg may also reappear during reactivation. Episodes of reactivation can be severe and can mimic acute viral hepatitis. Subjects in whom such reactivation is seen tend to be older and to have had chronic type B hepatitis for a longer period of time. (See Hoofnagle and Alter, "Chronic Viral Hepatitis" Chapter 7, pp. 97–114, part. pp. 98–102, in Vyas et al., eds., above.)

The diagnosis of chronic type B hepatitis is made by the finding of chronic elevations in serum aminotransferase levels (ALT) and persistence of HBsAg in the blood for at least 6 months. Most human subjects with active liver disease will also be positive for HBeAg. This serological marker is invariably present at the onset of the chronic HBsAg carrier state. With time, HBeAg may disappear and be replaced by anti-HBe. This seroconversion is usually, but not always, accompanied by a sustained decrease in the activity of the chronic liver disease. Those subjects with anti-HBe who have ongoing chronic liver disease typically have other serological evidence of active viral replication, either low and intermittent levels of HBV-DNA and DNA polymerase or hepatitis B core antigen in liver. Another serological marker for the presence of active HBV replication and accompanying chronic hepatitis disease activity is IgM anti-HBc. This antibody may be present when HBV-DNA, DNA polymerase and HBeAg are no longer detectable or are present in only low titer. See Hoofnagle and Alter, above, pp. 103–4.

Hoofnagle and Alter, above, at page 100, report that liver biopsies taken on 85 human subjects who were HBsAg positive for at least six months (but not yet positive for anti-HBe) showed chronic persistent hepatitis in 26 percent, chronic active hepatitis in 39 percent and chronic active hepatitis with cirrhosis in 20 percent, respectively, of said subjects.

An animal, particularly a primate such as man, infected with hepatitis B virus would receive one of two dose regimens.

Said subject would receive either (1) daily injection of the compound at a dose range of 1 to 20 mg/kg (body weight) for a period of 2 weeks or (2) daily oral administration of 10 to 50 mg/kg for one month (or for longer periods as determined by the subject's physician). To follow the state of disease, subjects wohuld be monitored with virological markers such as DNA polymerase (PNAS 77, 2941 [1980]) as well as HBsAg, HBeAg, antibody to HBsAg (Anti-HBs), and antibody to HBeAg (AntiHBe) (J. Infectious Diseases 148, 907 [1983]). The polymerase levels would be determined twice a week during the period. The other assays would be performed weekly. Serum glutamic oxaloacetic transaminase levels (SCOT) could also be monitored weekly. Alternately, serum alanine aminotransferase (ALT) and aspartate aminotransferase (AST) levels could also be monitored. The frequency and length of the drug administration and monitoring could be adjusted according to information obtained from the levels of virological markers.

Such course of treatment could be used in combination with other appropriate therapies.

The preparation of compounds (b)–(e) is illustrated by the following examples:

EXAMPLE 1

3-Amino-4-deoxo-4-((4-aminophenyl)sulfonyl)-aminorifamycin SV (b)

A solution of 2.6 g of sodium 4-aminobenzenesulfinate in 5 ml of water was added to a solution of 2.8 g of 3-Amino-4-deoxo-4-iminorifamycin S in 50 ml of dimethyl sulfoxide. The mixture was stirred at room temperature for 5 minutes and then poured into brine. After acidification with di. $H_2SO_4$, the reaction mixture was extracted with chloroform. The extract was washed with brine, dried over anhydrous sodium sulfate, and then evaporated. The residue was precipitated from chloroform-hexane to give 2.2 g of 3-Amino-4-deoxo-4-((4-amino-phenyl)sulfonyl)aminorifamycin SV as a yellow powder.

IR ($CHCl_3$): 1156 cm$^{-1}$ (sulfonamide).

The pmr spectrum ($CDCl_3$) shows the characteristic singlet signals of the methyl groups at $\delta 1.59$ (3H), 2.08 (6H), 2.14 (3H) and 3.02 (3H) ppm.

EXAMPLE 2

4-O-butylsulfonyl-3-(piperidinoimino)methyl-rifamycin SV (c)

A solution of 2.0 g of sodium butylsulfinate in 10 ml of water was added to a solution of 2.5 g of 3-(piperidinoimino)methylrifamycin S in 100 ml of N,N-dimethylformamide. The mixture was stirred at room temperature for 9 hours and then poured into brine. After acidification with dilute $H_2SO_4$, the reaction mixture was extracted with ethyl acetate. The extract was washed with brine, dried over anhydrous sodium sulfate, and then evaporated to dryness. The residue was subjected to silica gel column chromatography [solvent; chloroform-methanol (20:1)] and then recrystallized from ethyl acetate-hexane to give 1.5 g of 4-O-butylsulfonyl-3-(piperidinoimio)methylrifamycin SV as yellow crystals IR (KBr): 1165 cm$^{-1}$ (sulufonate).

The pmr spectrum ($CDCl_3$) shows the characteristic singlet signals of the hydrazonomethyl group at $\delta 8.02$ (1H) and those of the methyl groups at $\delta 1.78$ (3H), 2.06 (3H), 2.10 (3H), 2.28 (3H) and 3.06 (3H) ppm.

EXAMPLE 3

4-O-butylsulfonyl-3-(morpholinoimino)methyl-rifamycin SV (d)

A solution of 2.0 g of sodium butylsulfinate in 10 ml of water was added to a solution of 3.0 g of 3-(morpholinoimino)methylrifamycin S in 150 ml of dimethyl sulfoxide. The mixture was stirred at room temperature for 20 hours and then poured into brine. After acidification with dil. $H_2SO_4$, the reaction mixture was extracted with ethyl acetate. The extract was washed with birne, dried over anhydrous sodium sulfate, and then evaporated to dryness. The residue was subjected to silica gel column chromatography [solvent; chloroform-methanol (10:1)], and then recrystallized from ethylacetate-hexane to give 1.8 g of 4-O-butylsulfonyl-3-(morpholinoimino)methylrifamycin SV as yellow crystals.

IR (KBr): 1165 cm$^{-1}$ (sulfonate).

The pmr spectrum ($CDCl_3$) shows the characteristic singlet signals of the hydrazonomethyl group at $\delta 8.16$ (1H) and those of the methyl groups at $\delta 1.78$ (3H), 2.07 (3H), 2.12 (3H), 2.30 (3H) and 3.08 (3H) ppm.

EXAMPLE 4

3-(dimethylhydrazono)methyl-4-O-(3-phenylpropyl)-sulfonylrifamycin SV (e)

A solution of 3.0 g of sodium 3-phenylpropane sulfinate in 15 ml of water was added to a solution of 3.0 g of 3-(dimethylhydrazono)methylrifamycin S in 150 ml of dimethyl sulfoxide. The mixture was stirred at room temperature for 24 hours and then poured into brine. After acidification with dil. $H_2SO_4$, the reaction mixture was extracted with ethyl acetate. The extract was washed with brine, dried over anhydrous sodium sulfate, and then evaporated to dryness. The residue was subjected to silica gel column chromatography two times [solvent: chloroform-methanol (85:1), chloroform-acetone (4:1), respectively], and then recrystallized from ethylacetate-ligroin to give 0.7 g of 3-(dimethylhydrazono)methyl-4-O-(3-phenylpropyl)sulfonyl-rifamycin SV as yellow crystals IR (KBr): 1160 cm$^{-1}$ (sulufonate).

The pmr spectrum (CDCl$_3$) shows the characteristic singlet signals of the hydrazonomethyl group at δ7.66 (1H) and those of the methyl groups at δ1.68 (3H), 2.05 (3H), 2.08 (3H), 2.28 (3H), 2.95 (6H) and 3.03 (3H) ppm.

EXAMPLE 5

4-deoxy-N,3-ethylidenimino-4-(methylsulfonyl)amino-rifamycin SV (f)

(1) 3-amino-4-deoxy-4-(methylsulfonyl)aminorifamycin SV

A solution of 2.3 g of sodium methanesulfinate in 15 ml of water was added to a solution of 5.3 g of 3-amino-4-deoxy-4-iminorifamycin S in 90 ml of dimethyl sulfoxide. The mixture was stirred at room temperature for 10 minutes and then poured into brine. After acidification with dilute H$_2$SO$_4$, the reaction mixture was extracted with chloroform. The extract was washed with brine, dried over anhydrous sodium sulfate, and then evaporated. The residue was precipitated from chloroform-hexane to give 3.9 g of 3-amino-4-deoxy-4-(methylsulfonyl)aminorifamycin SV as a yellow powder.

IR (CHCl$_3$): 1155 cm$^{-1}$ (sulfonamide).

The pmr spectrum (CDCl$_3$) shows the characteristic singlet signals of the methyl groups at δ1.80 (3H), 2.08 (6H), 2.24 (3H), 2.63 (3H) and 3.07 (3H).

(2) 4-deoxy-N,3-ethylidenimino-4-(methylfulfonyl)amino-rifamycin SV

Two ml of acetaldehyde was added to a solution of 3.0 g of 3-amino-4-deoxy-4-(methylsulfonyl)aminorifamycin SV in 100 ml of tetrahydrofuran. The mixture was stirred at room temperature for 4 hours, and then evaporated to dryness. the residue was subjected to silica gel column chromatography [solvent; chloroform-methanol (50:1)], and then precipitated from chloroform-hexane to give 1.5 g of 4-deoxy-N,3-ethylidenimino-4-(methylsulfonyl)aminorifamycin SV as a yellow powder.

IR (CDCl$_3$): 1147 cm$^{-1}$ (sulfonamide).

The pmr spectrum (CDCl$_3$) shows the characteristic doublet signal of the methyl group of the ethidenimino group at δ1.49 (3H) and the characteristic singlet signals of the methyl groups at δ1.78 (3H), 2.09 (9H), 2.69 (3H) and 3.11 (3H).

What is claimed is:

1. A method of treating an animal infected by hepatitis B virus comprising administering to such infected animal an amount of the rifamycin derivative 4-deoxo-N,3-ethylidenimino-4-(methylsulfonyl)amino-rifamycin SV, said amount being effective to reduce the effects of said hepatitis B virus.

2. A method of claim 1 in which the amount of the rifamycin derivative administered is effective to inhibit the replication of the hepatitis B virus in said infected animal.

3. A method of claim 1 in which the animal is man or those primates known to be subject to infection by hepatitis B virus.

4. A method of inhibiting the viral polymerase of hepatitis B virus comprising subjecting said viral polymerase to an amount of the rifamycin derivative 4-deoxo-N,3-ethylidenimino-4-(methylsulfonyl)amino-rifamycin SV, said amount being effective to inhibit the replication of the hepatis B virus by said viral polymerase.

5. A method of preventing hepatitis in an animal suspected of having been infected with hepatitis B virus, said method comprising administering to said animal an amount of the rifamycin derivative 4-deoxo-N,3-ethylidenimino-4-(methylsulfonyl)amino-rifamycin SV, said amount being effective to inhibit the replication of said hepatitis B virus.

6. A method of claim 5 in which the animal is man or those primates known to be subject to infection by hepatitis B virus.

7. A rifamycin derivative selected from a group consisting of
   (b) 3-amino-4-deoxo-4-[(4-aminophenyl)sulfonyl]amino-rifamycin SV,
   (c) 4-O-(n-butylsulfonyl)-3-[(1-piperidinylimino)methyl]-rifamycin SV,
   (d) 4-O-(n-butylsulfonyl)-3-[(4-morpholinylimino)methyl]-rifamycin SV,
   (e) 3-[(dimethylhydrazono)methyl]-4-O-[(3-phenylpropyl)sulfonyl]-rifamycin SV, and
   (f) 4-deoxo-N,3-ethylidenimino-4-(methylsulfonyl)amino-rifamycin SV.

* * * * *